(12) United States Patent
Okazaki et al.

(10) Patent No.: US 10,094,752 B2
(45) Date of Patent: Oct. 9, 2018

(54) FOLDING TEST MACHINE

(71) Applicant: YUASA SYSTEM CO., LTD., Okayama-shi, Okayama (JP)

(72) Inventors: Yasuhisa Okazaki, Okayama (JP); Naotsugu Ando, Okayama (JP); Hisao Sasaki, Okayama (JP)

(73) Assignee: Yuasa System Co., Ltd., Okayama-shi (JP)

( * ) Notice: Subject to any disclaimer, the term of this patent is extended or adjusted under 35 U.S.C. 154(b) by 417 days.

(21) Appl. No.: 14/879,395

(22) Filed: Oct. 9, 2015

(65) Prior Publication Data

US 2016/0103048 A1   Apr. 14, 2016

(30) Foreign Application Priority Data

Oct. 11, 2014  (JP) ................................. 2014-209544
Sep. 15, 2015  (JP) ................................. 2015-181302

(51) Int. Cl.
*G01N 3/20*      (2006.01)
*G01N 3/32*      (2006.01)

(52) U.S. Cl.
CPC .................. *G01N 3/20* (2013.01); *G01N 3/32* (2013.01); *G01N 2203/0005* (2013.01); *G01N 2203/0023* (2013.01); *G01N 2203/0282* (2013.01)

(58) Field of Classification Search
CPC .. G01N 3/20; G01N 3/32; G01N 3/04; G01N 3/36; G01N 2203/0005; G01N 2203/0023; G01N 2203/0282
See application file for complete search history.

(56) References Cited

U.S. PATENT DOCUMENTS

2011/0248739 A1*  10/2011  Kim ...................... G01M 5/005
                                                   324/762.01

FOREIGN PATENT DOCUMENTS

JP          4238774       *  3/2009   ............... G01N 3/34
JP      A 2013-057538        3/2013
JP      A 2013-064658        4/2013

* cited by examiner

*Primary Examiner* — Blake A Tankersley
(74) *Attorney, Agent, or Firm* — Trojan Law Offices

(57) ABSTRACT

A folding test machine to measure the durability against folding can be operated by minor adjustment even if a radius of curvature of the folding or an arc length of the folding is changed. A fixed wall and a moveable wall are opposingly provided in an approximately box-shaped frame and a holding part to hold a workpiece is provided on the top of each of the fixed wall and the moveable wall in a rotatable manner in a vertical plane of the rotation. And the workpiece and a plate spring are held on the respective opposing end portions so as to be bridged between the fixed wall and the moveable wall in a curved manner such that the moveable wall is moved closer to and farther from the fixed wall repeatedly such that the work is folded repeatedly.

14 Claims, 4 Drawing Sheets

FOLDING TEST MACHINE

FIELD OF THE INVENTION

The present invention relates to a folding test machine to test durability of a thin glass plate or resin plate utilized for a flexible display such as a substrate of a mobile phone and the like and an organic light-emitting diode and the like by bowing (folding, bending, or bowing) the thin glass plate or resin plate.

BACKGROUND ART

A recent mobile phone has become thinner and thinner. According to this trend, a substrate used therein, of course, also has become thinner. However, as the mobile phone becomes thin, a curvature of a folded substrate becomes too much such that the substrate may be damaged. Here, the curvature generally means being folded in a bow-shaped manner and, in particular, it signifies an evenly-curved curvature of a bend (for example, the bend having the radius of the curvature continuously and smoothly changing) and the above-mentioned substrate and the like may be used under such a curvature condition. Hence, the test is conducted before the actual use, but it is an issue if the substrate works in a normal way or not especially when the substrate is folded in the bow-shaped manner. It has been conventionally judged whether the substrate is appropriate or not by bending the substrate in the bow-shaped manner by hand. However, it is not efficient to conduct such a test by hand for each substrate with respect to each different curvature radius of the curvature and each different arc length (length of a bent portion).

Although the folding itself can be conducted by a machine if it is wished to use the machine, the folding test may not be able to be conducted depending on the way of conduction.

Unexamined laid-open Japanese patent application No. 2013-057538 discloses a device which conducts the folding by the machine. However, the device shown in the reference is to simply bend a specimen to be examined, but not to bend the specimen to have the evenly-curved curvature of the bend, although the device relates to bending of a planar body. And the device is not a test device to test the specimen by changing the curvature radius of the bend.

SUMMARY OF THE INVENTION

In the present invention, an apparatus for realizing this type of folding test by the machine is provided whereby the machine can operate with minimized adjustment even if the curvature radius or the arc length of the bend is changed.

Under the above-mentioned situation, according to an aspect of the present invention, a folding test machine is to be provided in which a fixed wall and a moveable wall are arranged in an opposing manner inside a frame shaped in an approximately boxed-shape; holding parts to hold a workpiece (for example, a physical object to be tested by the present test machine) at top portions of the respective walls are arranged in a rotatable manner in a vertical plane perpendicular to the fixed wall and the moveable wall; and the workpiece and a plate spring other than the object are held by the holding parts on the both ends thereof so as to be bridged between the fixed wall and the moveable wall in a bow-shaped manner such that the folding test machine is characterized in that the workpiece may be bent repeatedly in the bow-shaped manner by moving the moveable wall closer to and farther from the fixed wall over and over.

According to another aspect of the present invention, the both walls are moveable walls to be able to move so as to provide the configuration in which both walls are moved closer to and farther from each other or, while one wall is fixed, the other wall is moved closer to and farther from the one. Further, according to yet another aspect, the configuration in which plate springs are provided to both sides of the workpiece is provided wherein lengths of the spring plates are the same as the workpiece.

According to an aspect, the workpiece such as a thin glass plate or resin plate is bridged between the fixed wall and the moveable wall in a bow-shaped manner such that the workpiece may be repeatedly bent in the bow-shaped manner by moving the moveable wall closer to and farther from the fixed wall over and over. In this embodiment, a shape factor such as a curvature radius of the bent portion of the workpiece may be changed, which is enabled by changing a length of a stroke of an actuator to move the moveable wall and initial positions of both walls. Also, the holding parts to hold the workpiece are so configured as to be arranged in a rotatable manner (in a tiltable manner to the opponent) in a vertical plane perpendicular to the fixed wall and the moveable wall such that the folding test machine may be competent to cope with the change of the length of the stroke without leaving internal stress therein. Further, it is preferable to adjust the speed of bending in the bow-shaped manner and it can be achieved by changing the speed of the actuator.

According to another aspect, it is possible to change the applicable manner and the shape factor such as types of bending in a bow-shaped manner and a curvature radius in a variety of ways by moving both the fixed wall and the moveable wall.

DESCRIPTION OF THE PREFERRED EMBODIMENT

Figure 1:
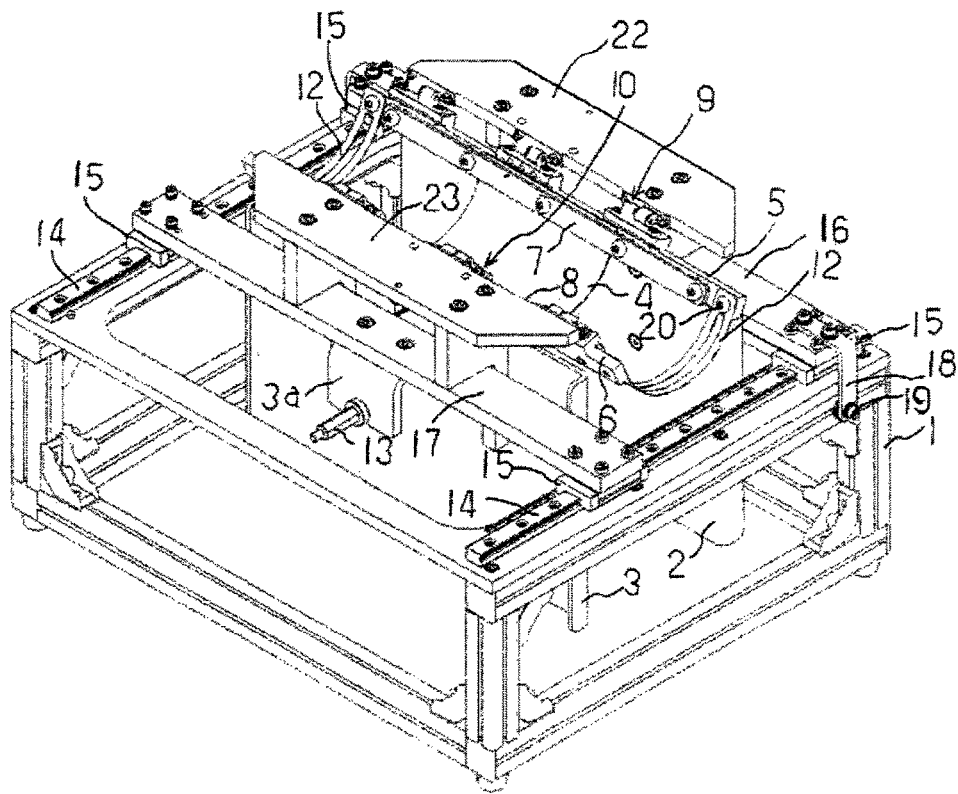
FIG. 1 shows a perspective view of a folding test machine.
Figure 2:
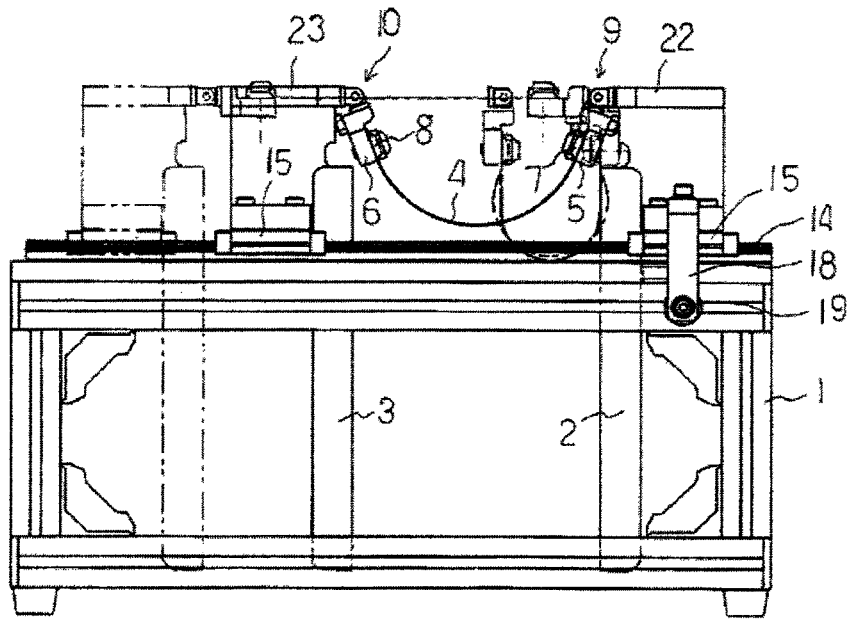
FIG. 2 shows a side view of the folding test machine.

In the following, a structure of an embodiment of the present invention is explained with reference to the drawings. FIG. 1 shows a perspective view of a test machine according to the present invention. In a frame 1 shaped in an approximately boxed-shape, a fixed wall 2 is provided in a vertical manner on one end side and a moveable wall 3 is provided in a vertical manner in a middle position wherein the respective walls are arranged in an opposing manner. Here, the fixed wall 2 is fixed to the frame with a fixing device such as a bolt. The moveable wall 3 is so arranged in a moveable manner as to be moved by an external force closer to and farther from the fixed wall 2 side over and over.

Hence, a flap portion extended lower 3a is provided with a connecting portion 13 to which an actuator such as a cylinder and the like may be connected such that the actuator (not shown in the drawings) is connected to this. Any kinds of known devices may be adaptively applied to the actuator such that the actuator may include a piston to make a reciprocating motion. Here, FIG. 1 shows a main configuration part to cause the bending in the bow-shaped manner of the folding test machine.

A well-known structure, in fact, may realize fixing the fixed wall 2 and moving the moveable wall 3. In the present embodiment, a pair of rails 14 are provided on both sides of the frame 1 as the respective rails 14 extend from one end side to the opposing other end side in the direction approximately perpendicular to the fixed wall 2 wherein said both sides comprise respective frame members connecting the one side end and the other side end of the frame 1. With respect to the respective rails 14, sliders 15 are moveably mounted on the respective rails. A bar 16 aligned with the fixed wall 2 is bridged between the sliders mounted at the opposing positions on the respective rails 14. In the same way, a bar 17 aligned with the moveable wall 3 is bridged between the sliders mounted at the opposing positions on the respective rails 14. Here, the fixed wall 2 is not supposed to move relative to the frame 1 such that a bracket 18 is extended lower from the bar 16 outside of each side face of each of both sides of the frame 1 and the bracket 18 is fixed to the frame with a screw 19 or the like. Thus, the moveable wall 3 moves closer and farther with respect to the fixed wall 2 as the actuator of the moveable wall 3 is operated. Here, when the position of the fixed wall 2 is changed, the position of the bracket 18 may be changed by adjusting the screw 19 or the like.

On the bar 16, a pair of plate-shaped pillars are built approximately vertically and aligned to the longitudinal direction and a ceiling plate 22 is fixed on the top of the pillars. The ceiling plate 22 extends approximately parallel to the bar 16 in the longitudinal direction and appears trapezoid in a top view wherein an inside end portion facing the moveable wall 3 is longer than the opposing outside end portion. A hinge 9 is provided to the inside end portion. In the same way, on the bar 17, a pair of plate-shaped pillars are built approximately vertically and aligned to the longitudinal direction and a ceiling plate 23 is fixed on the top of the pillars. The ceiling plate 23 extends approximately parallel to the bar 17 in the longitudinal direction and appears trapezoid in a top view wherein an inside end portion facing the fixed wall 2 is longer than the opposing outside end portion. A hinge 10 is provided to the inside end portion.

An workpiece 4 having an approximately rectangular plate shape is bridged between the moveable wall 3 and the fixed wall 2 (hereinafter, the dimension in the bridging direction in the plan view is referred to the length of the workpiece 4 and the dimension in the direction approximately perpendicular to the bridging direction is referred to as the width of the workpiece 4). At this time, the workpiece 4 is mounted on the moveable wall 3 by clamping it between a holding part 6 fixed to the ceiling plate 23 in a rotatable manner in a vertical plane due to the hinge 10 and a pressing plate 8 fixed to the holding part 6 wherein the ceiling plate 23 is provided on the summit (top end) side of the moveable wall 3. In the same way, the workpiece 4 is mounted on the fixed wall 2 by clamping it between a holding part 5 fixed to the ceiling plate 22 in a rotatable manner in a vertical plane due to the hinge 9 and a pressing plate 7 fixed to the holding part 5 wherein the ceiling plate 22 is provided on the summit (top end) side of the fixed wall 2. That is, the holding parts 5, 6 fixed by the hinges 9, 10 in the rotatable manner may be tilted (or rotated) toward the opponent as the fixed wall 2 and the moveable wall 3 are moved closer to and farther from each other. Since both end portions of the workpiece 4 are held by both holding parts 5, 6, angles of inclinations of both end portions of the workpiece 4 are changed depending on the curvature radii caused by the bending of the workpiece 4. As the holding parts 5, 6 can be tilted (or rotated), the situations may be accommodated well. The above-mentioned configuration is also aimed to minimize local stress or stress concentration that may be caused inside of the workpiece 4.

Figure 3A:
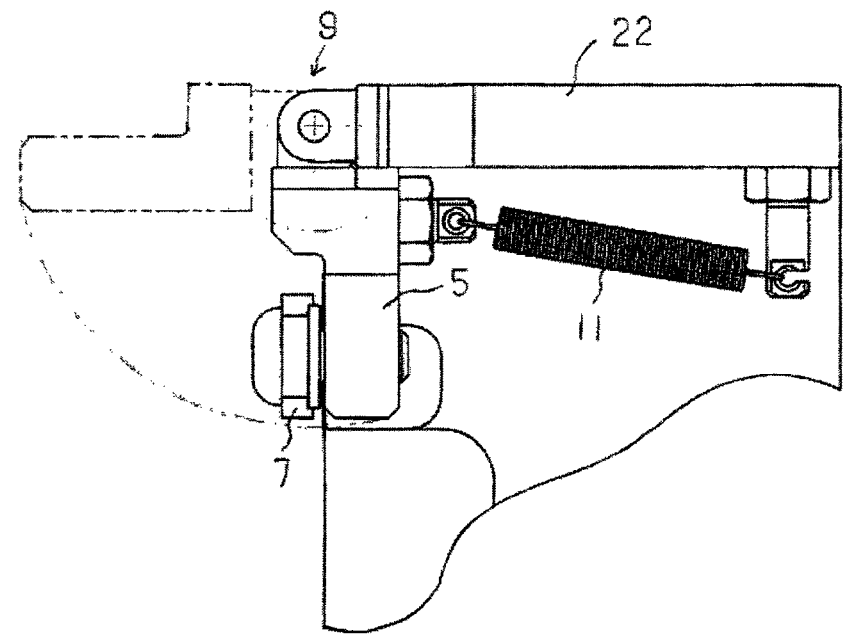
FIG. 3A shows an enlarged side view of a vicinity of a holding part.
Figure 3B:
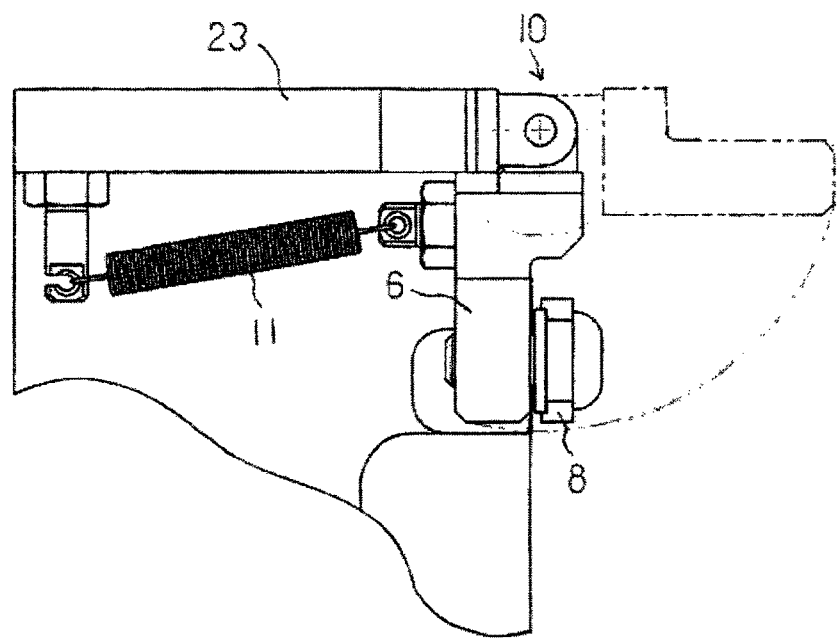
FIG. 3B shows an enlarged side view of a vicinity of a holding part.

The hinges 9, 10 are so devised as to have lighter weight and less friction resistance of rotation. Here, the workpiece 4 has the weight such that a bowed-shape thereof sagging down more or less is formed when the moveable wall 3 and the fixed wall 2 are separated by the distance of almost the length of the workpiece 4. FIGS. 3A and 3B show side views of main parts. The holding parts 5, 6 are pulled to the lower direction by springs 11. This is to prevent the holding parts 5, 6 from being lifted up higher than the horizontal line due to the inertia such that speeding-up of the operation can be performed. Here, in the test by the present test machine, it is not preferable that the moveable wall 3 moves away from the fixed wall 2 by more than the distance when the workpiece 4 is bridged. This is because a tensile force may be applied to the workpiece 4.

Further, outside of both side end portions of the workpiece 4 other than the two end portions fixed to the holding parts 5, 6 arranged in an opposing manner, plate springs 12 having the same length as the workpiece 4 are so held by the holding parts 5, 6 with bolts 20 as to be bridged. The plate spring 12 is so characterized as to tend to have an evenly-curved curvature radius when it is bent in a bow-shaped manner whereby each of the holding parts 5, 6 is tilted (or rotated) in an optimum angle to realize the evenly-curved curvature. Thus, the workpiece is also bent in the bowed shape with an evenly-curved curvature radius since the workpiece is held by the holding parts 5, 6 with angles of tilt (or inclination angles). That is, the curvature of the workpiece 4 may be aligned to the curvature of the plate spring 12 and the workpiece 4 may be bent in the bow-shaped manner evenly by providing the plate springs 12 on outsides of both sides of the workpiece 4. In this embodiment, it is preferable that the plate spring 12 has higher endurance than that of the workpiece 4. It is also preferable that the resistive force of the plate spring 12 against the bending is higher than the resistive force of the workpiece 4.

Figure 4:
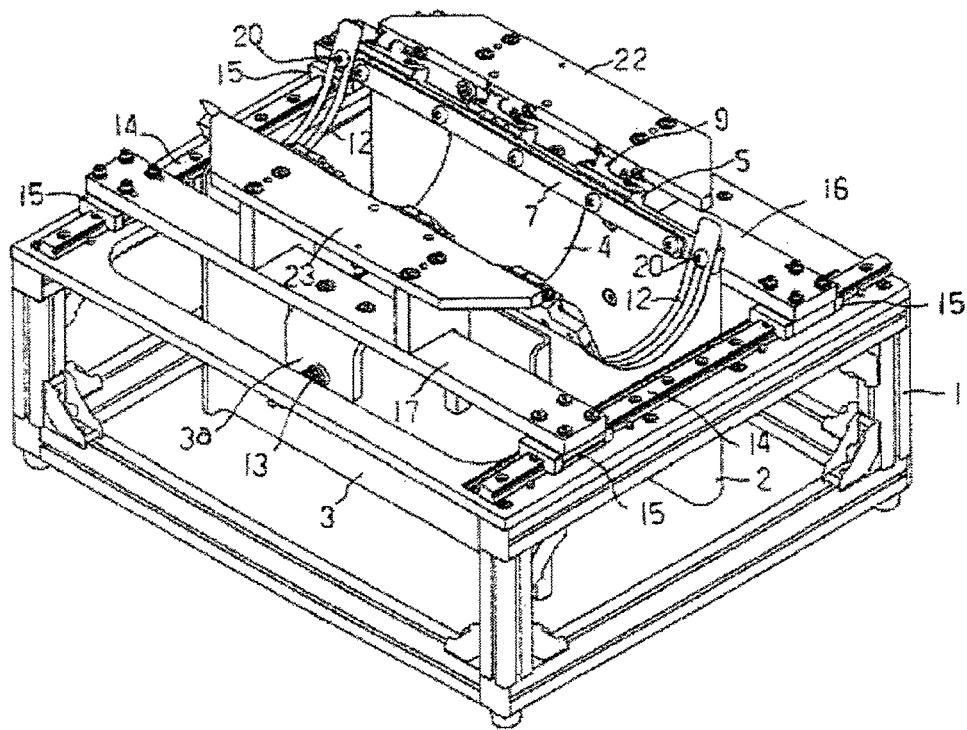
FIG. 4 shows a perspective view of another example of the folding test machine.
Figure 5:
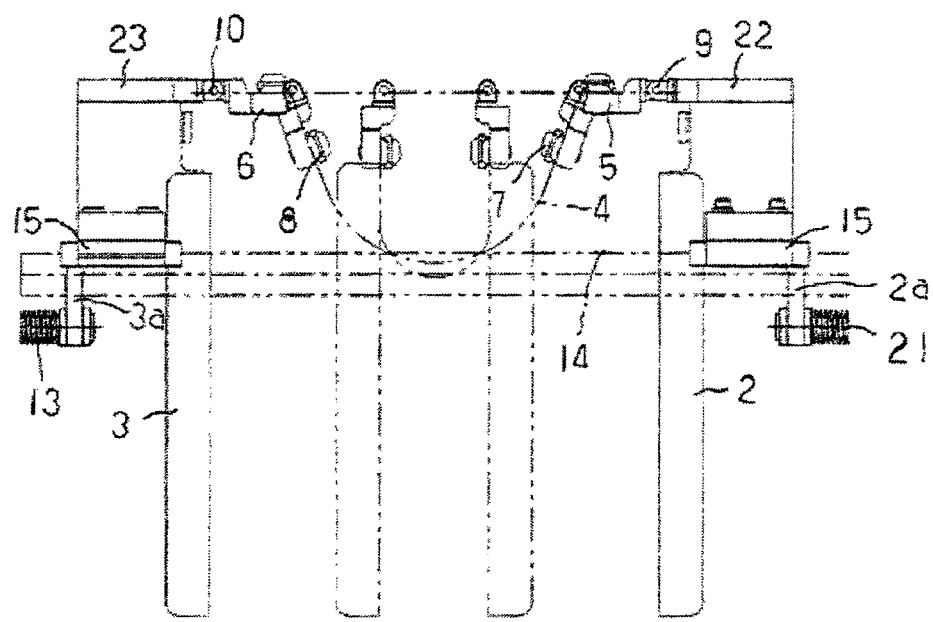
FIG. 5 shows a perspective view of another example of the folding test machine.

In the aforementioned, a basic configuration of the present invention is described, but the configuration may be modified in other ways. A modified configuration is typically described to have the fixed wall 2 move in a similar way as the moveable wall 3 moves. As it is shown in FIGS. 4 and 5, a connecting portion 21 is formed on a flap portion extended lower 2a instead the bracket 18 and the screw 19 for the fixed wall 2 and an actuator is connected to the connecting portion 21. Thus, the fixed wall 2 is moved together with the moveable wall 3 when the two actuators are operated at the same time. In this embodiment, it is possible to include a variety of configuration of the test by changing the moving speed and the stroke distance or direction of the respective actuators.

Further, it is also possible to conduct a test in which only either wall is moved if the other wall is locked (the position at which the other wall is locked is configured to be changeable).

Figure 6:
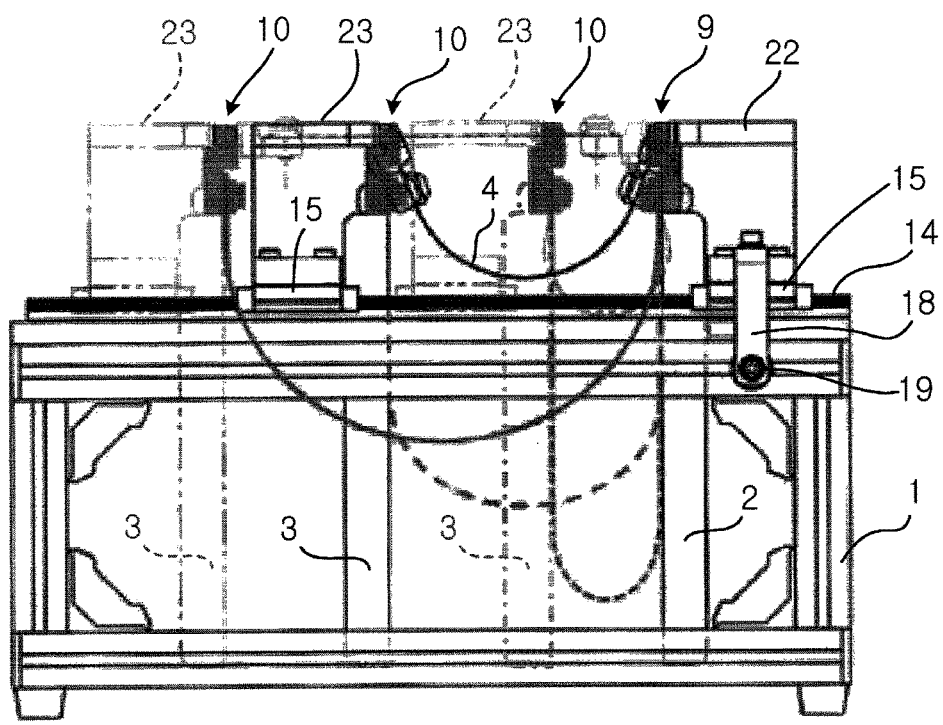
FIG. 6 shows a side view of the folding test machine in which a situation where a workpiece is largely bend in a bow-shaped manner is included.

Further, the folding test machine of the present embodiment of the present invention can bend the workpiece 4 into the largely-bowed shape. For example, as shown in FIG. 6, the holding parts 5, 6 are directed downward almost in the vertical direction and the workpiece 4 is contacted on the fixed wall 2 and the moveable wall 3 such that the curvature of the workpiece 4 can be controlled to be in a U-shape. And, the fixed wall 2 and the moveable wall 3 can prevent broken pieces of the workpiece 4 from flying apart even if the workpiece 4 is broken during the endurance test. For example, the fixed wall 2 and the moveable wall 3 may have length about one half of the length of the workpiece 4.

What is claimed is:

1. A folding test machine comprising:
   a fixed wall and a moveable wall arranged in an opposing manner inside the frame shaped in an approximately boxed-shape;
   a first holding part provided on a top of the fixed wall;
   a second holding part provided on a top of the moveable wall;
   a workpiece, a first end of which is held by the first holding part and a second end of which is held by the second holding part, wherein the workpiece in a plate shape is bridged between the first holding part and the second holding part; and
   a first plate spring provided beside a first side of the workpiece, the first plate spring being bridged between and held by the first holding part and the second holding part;
   wherein the workpiece and the first plate spring are bridged between the fixed wall and the moveable wall such that the workpiece is bent in a curved manner repeatedly in a same way as the first plate spring is bent during reciprocating movement of the moveable wall from the fixed wall.

2. The folding test machine according to claim 1 wherein the movable wall, while the fixed wall is fixed, is capable of moving such that the fixed wall and the moveable wall get closer and farther with each other.

3. The folding test machine according to claim 2 comprising: a second plate spring provided beside a second side of the workpiece and bridged between the moveable wall and the fixed wall wherein the first plate spring and the second plate spring are disposed on outsides of both side portions of the workpiece.

4. The folding test machine according to claim 1 comprising: a second plate spring provided beside a second side of the workpiece and bridged between the moveable wall and the fixed wall wherein the first plate spring and the second plate spring are disposed on outsides of both side portions of the workpiece.

5. A folding test machine to repeatedly fold a workpiece shaped in a plate comprising:
   a frame shaped in an approximately boxed-shape;
   a first workpiece holding part fixed to the frame;
   the workpiece, a first end side of which is held by the first workpiece holding part;
   a second workpiece holding part arranged in an opposing manner to the first workpiece holding part and disposed in a moveable way to the frame, the second workpiece holding part holding a second end side of the workpiece in a length direction thereof;
   a plate spring provided beside a first side of the workpiece, held in the length direction between the first workpiece holding part and the second workpiece holding part, and held by the first workpiece holding part and the second workpiece holding part; and
   an actuator connecting portion to be driven to move the second workpiece holding part closer to and farther from the first workpiece holding part;
   wherein the first workpiece holding part and the second workpiece holding part are configured to be rotatable in a plane that includes a direction of the movement; and
   wherein the workpiece is bent in a curve manner repeatedly in a same way as the platespring is bent during reciprocating movement of the first workpiece holding part relative to the second workpiece holding part.

6. The folding test machine according to claim 5 wherein the first workpiece holding part and the second workpiece holding part comprise elastic members to prevent the workpiece from bouncing back by back action of the workpiece bent in a bow-shaped manner repeatedly.

7. The folding test machine according to claim 5 wherein the second workpiece holding part is mounted on a slider provided in a moveable manner on a rail provided on the frame.

8. The folding test machine according to claim 5 comprising: another plate spring provided beside another side of the workpiece and bridged between the first workpiece holding part and the second workpiece holding part.

9. A folding test machine comprising:
   a frame shaped in an approximately boxed-shape;
   a first wall and a second wall arranged in an opposing manner inside the frame;
   a first holding part provided in a rotational manner in a vertical plane on a top of the first wall;
   a sample of a plate shape, one end of which is held by the first holding part;
   a second holding part provided in a rotational manner in a vertical plane on a top of the second wall, the second holding part holding another end of the sample in a length direction thereof;
   a plate spring provided beside one side of the sample wherein the first holding part holds one end of the plate spring and the second holding part holds the other end of the plate spring such that the plate spring in a plate shape is bridged between the first holding part and the second holding part; and the sample and the plate spring are bridged between the first wall and the second wall in a curved manner such that the sample is bent in a curved manner repeatedly in a same way as the plate spring is bent during reciprocating movement of the first wall from the second wall.

10. The folding test machine according to claim 9 wherein the first wall is capable of moving together with the second wall such that the first wall and the second wall get closer and farther with each other.

11. The folding test machine according to claim 10 comprising a second plate spring having a same length as the sample is provided beside a second side of the sample and bridged between the first holding part and the second holding part.

12. The folding test machine according to claim 9 wherein either the first wall or the second wall is capable of moving, while the other wall is fixed, such that the first wall and the second wall get closer and farther with each other.

13. The folding test machine according to claim 12 comprising a second plate spring having a same length as the sample is provided beside a second side of the sample and bridged between the first holding part and the second holding part.

14. The folding test machine according to claim 9 comprising: another plate spring provided beside another side of the sample and bridged between the first wall and the second wall.

\* \* \* \* \*